United States Patent
Tasar et al.

(10) Patent No.: US 11,950,905 B2
(45) Date of Patent: Apr. 9, 2024

(54) DEVICE FOR MEASURING A PHYSIOLOGICAL PARAMETER OF A HUMAN LIMB AND METHOD FOR MANUFACTURING SUCH DEVICE

(71) Applicant: KONINKLIJKE PHILIPS N.V., Eindhoven (NL)

(72) Inventors: Ozgur Tasar, Eindhoven (NL); Lieven Adriaenssen, Vilvoorde (BE); Job Lipsch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 660 days.

(21) Appl. No.: 16/633,238

(22) PCT Filed: Jul. 26, 2018

(86) PCT No.: PCT/EP2018/070296
§ 371 (c)(1),
(2) Date: Jan. 23, 2020

(87) PCT Pub. No.: WO2019/020749
PCT Pub. Date: Jan. 31, 2019

(65) Prior Publication Data
US 2021/0128034 A1 May 6, 2021

(30) Foreign Application Priority Data

Jul. 26, 2017 (EP) .................................... 17183291

(51) Int. Cl.
*A61B 5/1455* (2006.01)
*A61B 5/00* (2006.01)

(52) U.S. Cl.
CPC .......... *A61B 5/14552* (2013.01); *A61B 5/683* (2013.01); *A61B 2562/12* (2013.01)

(58) Field of Classification Search
CPC .............................. A61B 5/1455; A61B 5/683
See application file for complete search history.

(56) References Cited

U.S. PATENT DOCUMENTS 5,035,243 A    7/1991  Muz
6,385,821 B1*  5/2002  Modgil ............... A61B 5/6826
                                          24/304

(Continued)

FOREIGN PATENT DOCUMENTS

CN    102421361 B    4/2012
GB      2259545 A    3/1993

(Continued)

OTHER PUBLICATIONS

International Search Report and Written Opinion, International Application No. PCT/EP2018/070296, dated Nov. 14, 2018.

*Primary Examiner* — Marjan Fardanesh (57) ABSTRACT

The present invention relates to a device for measuring a physiological parameter of a human limb such as peripheral capillary oxygen saturation. The device comprises a hollow elastic sleeve of a predetermined shape comprising a cavity having a closed-loop cross-section for enclosing the limb; first and second arms, each comprising a hinge portion between a coupling portion and a handle portion, the coupling portion of the first and second arms being adapted to be coupled, respectively, to first and second diametrically-opposite longitudinal sections of the sleeve; and a physiological sensor for interacting with the limb enclosed in said cavity. The hollow elastic sleeve holds the first and the second arms and causes their hinge portions to mutually engage to form a hinge mechanism so that, by applying a compression force on the handle portions, the first and second arms rotate about the hinge mechanism expanding the cavity, allowing the limb to be received therein. More- (Continued)

over, the hinge portions, when mutually engaged, are further configured to slide relative to each other.

20 Claims, 7 Drawing Sheets

(56) References Cited

U.S. PATENT DOCUMENTS

| | | |
|---|---|---|
| 6,580,086 B1 | 6/2003 | Schulz |
| 9,743,867 B2 | 8/2017 | Fujii |
| 2001/0009265 A1 | 7/2001 | Schulz et al. |
| 2015/0219129 A1 | 8/2015 | Gal |

FOREIGN PATENT DOCUMENTS

| | | |
|---|---|---|
| JP | 2007135718 A | 6/2007 |
| WO | 2011088621 A1 | 7/2011 |

\* cited by examiner

DEVICE FOR MEASURING A PHYSIOLOGICAL PARAMETER OF A HUMAN LIMB AND METHOD FOR MANUFACTURING SUCH DEVICE

This application is the U.S. National Phase application under 35 U.S.C. § 371 of International Application No. PCT/EP2018/070296, filed on 26 Jul. 2018, which claims the benefit of European Application Serial No. 17183291.8, filed 26 Jul. 2017. These applications are hereby incorporated by reference herein.

FIELD OF THE INVENTION

The present invention relates to an improved device for measuring a physiological parameter of a human limb that is easy to use and that makes it possible to measure the physiological parameter reliably for human limbs of different sizes. The present invention also relates to a method for manufacturing such device.

In particular, the present invention relates to measuring the oxygen saturation in a non-invasive manner, especially by pulse oximetry on a limb of the human body by use of a pulse oximeter which illuminates the skin and measures changes in light absorption.

BACKGROUND OF THE INVENTION

Pulse oximetry is a technique to assess the peripheral capillary oxygen saturation ($SpO_2$) of blood in a non-invasive manner using an emitted and detected light signal. Since its introduction in the clinic in the 1980's, this technique has become a standard of care in various clinical settings.

Pulse oximetry is generally measured at a fingertip, because the pulsatile optical signal is very strong at this location, and the body site is easy to access. However, other locations on the body are also suitable (e.g. forehead, toe, or ear lobe). Typically, a pulse oximetry probe operates in a so-called transmission geometry, in which a red and infrared light signals are transmitted into the subject's finger by two light-emitting diodes (LEDs), and the scattered light is detected by a light detector (such as for instance a photodiode) at the other side of the finger. Cardiac-induced pulsations in the blood volume manifest themselves as pulsations in the detected light intensity, and the blood oxygen saturation is derived from the ratio of pulse amplitudes in the red and infrared light intensity, where the relationship results from a difference in color of oxygen-bound and oxygen-unbound hemoglobin. For an accurate measurement, the architecture of the probe must be such that it prevents ambient light from reaching the light detector.

Alternatively to the use of LEDs, the light can also be brought to the probe via one or more fibers, for instance one or more optical fibers. In this case, the light source is preferably the end of the fiber. There also may exist pulse oximeters using more than 2 wavelengths, in particular 3, 4, 5, 6, 7 or 8 wavelengths.

A common way of securing a pulse oximetry probe to a finger or a toe of a patient is by means of the so-called "cloth peg" mechanism, also known as "finger clip", in which the probe is shaped as a clip or tweezer that clamps onto the finger or toe to perform the measurement. By compressing a handle, the clip-shaped probe opens up, enabling the finger or toe to be received in the space defined therebetween. Then, fixation of the probe on the finger or toe occurs automatically upon release of the handle. Other types of attachment mechanisms include the use of a flexible sleeve (or glove), or an adhesive wrap.

For example, U.S. Pat. No. 5,035,243 discloses a holder sleeve locking a detecting and measuring sensor into position, especially a detecting and measuring sensor for oximetric measurements, on the surface of a protruding part of a human body. The sensor includes a light source and a receiver which is sensitive to its radiation. The sleeve is elastically expandable and completely surrounds the body protruding part. Each of two diametrically opposite sections of the sleeve has a recess opening to the sleeve inside surface or is radiation-permeable to receive and hold the transmitter or the receiver. Both portions of the sleeve lying between these sections have pluralities of folds following one another around the sleeve periphery, with each fold forming a spring.

Current commercially-available probes suit adults' limbs in view of their size. However, probes designed for adults' limbs poorly fit on infants' limbs, which are significantly smaller than those of adults and have a much wider range of varying sizes (especially in the 0 to 60 month age range).

The major drawback of known pulse oximetry probes is, therefore, the problem of the different sizes in the limbs of infants of different age groups compared to the limbs of adults. Probes using the aforementioned "cloth peg" or flexible sleeve mechanisms are only suitable for a small range of infants and may easily be misplaced by untrained personnel. For example, for smaller finger or toe sizes the alignment of the finger or toe relative to the light source and the light detector of the pulse oximeter is prone to variation (i.e., incorrect placement) resulting in incorrect $SpO_2$ values. Even worse, if an infant's fingers or toes are too small, a clinician may instead try to attach the probe on the infant's ear, hand palm or foot, leading to an incorrect measurement and possibly to wrong diagnosis and treatment.

Although the sleeve-mechanism described in the aforementioned U.S. patent document would allow a larger variety of limb sizes, such a mechanism has the drawback that its placement on the patient's limb cannot be done using one hand only. Moreover, the sleeve the caregiver may be tempted to hold the limb while measuring, which leads to motion artifacts in the signal and inaccurate readings.

This makes it necessary to use a specific tailored-size probe for infants of a particular age group. In that regard, different pulse oximetry probes for infants characterized by their sizes are currently on the market such as to ensure not only comfort of the probe, but also the generation of a robust signal (e.g. measurement signal) of adequate quality and stability. However, a solution requiring a health worker to use probes of different sizes depending on the infants' age is far from ideal, especially in very low-resource settings and/or when the health worker has limited medical training.

It is therefore an object of the present invention to provide an improved device for measuring a physiological parameter of a human limb that is suitable for humans of different age groups, in particular infants in the age range of 0-60 months, while being easy to use and allowing accurate measurement after installation.

SUMMARY OF THE INVENTION

This object is solved by the device for measuring a physiological parameter of a human limb of claim 1 and by the method for manufacturing a device for measuring a physiological parameter of a human limb of claim 15.

Advantageous embodiments are defined in the dependent claims. It shall be understood that the claimed method has similar and/or identical preferred embodiments as the claimed device and as defined in the dependent claims.

An aspect of the present invention relates to a device for measuring a physiological parameter of a human limb, such as for instance a finger or a toe, comprising a hollow elastic sleeve comprising a cavity adapted to enclose the limb, the cavity extending longitudinally between a distal end and a proximal end and having a closed-loop cross-section. The hollow elastic sleeve has a predetermined shape to which the sleeve returns due to its resilience when an external force deforming the sleeve ceases to be applied thereto. The device further comprises a first and a second arm, each arm comprising a hinge portion located at an intermediate position of the arm between a coupling portion and a handle portion. The coupling portion of the first and the second arm are adapted to be coupled, respectively, to a first and a second longitudinal section of the hollow elastic sleeve from said proximal end, the first and second longitudinal sections being diametrically opposite to each other along a clamping direction extending across the cross-section of the cavity. The device also comprises a physiological sensor arranged within the cavity of the hollow elastic sleeve and configured for interacting with the limb enclosed in said cavity.

In accordance with the present invention, when the first and the second arms are coupled to the hollow elastic sleeve, the hollow elastic sleeve holds the first and the second arms and causes the hinge portions of the first and the second arms to engage each other to form a hinge mechanism so that, by applying a compression force on the handle portion of the first and second arms, the first and second arms rotate relative to each other about the hinge mechanism expanding the cross-section of the cavity at said distal end, thereby allowing the limb to be received in the cavity through said distal end, and, by ceasing said compression force, the resilience of the hollow elastic sleeve causes the first and second arms to rotate relative to each other in the opposite direction than following compression, thereby enclosing the limb in the cavity. Moreover, the hinge portions of the first and second arms, when engaged to each other, are further configured to slide relative to each other, so that the separation between the first and second arms along said clamping direction can be adjusted.

The present invention achieves an improved device for measuring a physiological parameter, in particular $SpO_2$ of blood, of a human limb which can be built with a plurality of alternative designs. The present invention is not restricted to measuring $SpO_2$, but can also be applied to measuring other physiological parameters such as pulse rate, dyshaemoglobin fractions (e.g. carboxy-hemoglobin and methemoglobin), electrocardiogram, pulse arrival time and blood sugar. In particular, the present invention may be integrated in a pulse oximeter.

In absence of external force, the hollow elastic sleeve remains in its non-deformed predetermined shape. In such state, the hollow elastic sleeve is capable of holding, by itself, the first and the second arms in a predetermined spatial relation with respect to each other, and causing the hinge portions of the first and the second arms to engage each other to form a hinge mechanism.

The hinge mechanism formed by the mutual engagement of the hinge portions of the two arms makes it possible to rotate one arm with respect to the other when a compression force is applied on the handle portions of the two arms. As the compression force exceeds the resetting force of the hollow elastic sleeve, the coupling portions of the two arms are rotated away from each other, which in turn expands the cross-section of the cavity near its distal end, facilitating a loose insertion of the limb into the cavity from said distal end. By ceasing the compression force once the limb has been inserted to a desired depth along the cavity, the resilience of the hollow elastic sleeve exerts a resetting force on the coupling portions of the two arms that brings them closer to each other, closing in the cross-section of the cavity near its distal end and securing the inserted limb in place. Moreover, by using hinge portions which are slidable relative to each other while engaging each other, the separation between the two arms along the clamping direction can be advantageously modified, making it possible to adjust the size of the cross-section of the cavity to match the size of the infant's limb.

From a mechanical standpoint, the arrangement of the hollow elastic sleeve and the hinge portions of the first and second arm works as a "snake jaw" hinge, or as a loose hinge without axle, in which the two hinge portions can slide relative to each other while still remaining loosely engaged thanks to the hollow elastic sleeve. Thus, the device of the present invention can advantageously adjust the size of the cross-section of the cavity of the hollow elastic sleeve to limbs of infants of a much wider range of ages (from neonates to older children) than the known devices in the prior art, being a truly "one-fits-all-sizes" type of device.

Therefore, the hollow elastic sleeve of the device of the present invention makes it possible to obtain a simple architecture in which no further support elements are needed to keep the first and the second arm in place. By causing the hinge portions of the first and the second arms to engage each other to form a hinge mechanism, the hollow elastic sleeve also makes it unnecessary to have to use an axle and/or additional guiding elements to enable the rotation and the sliding movement of the first and the second arms relative to each other.

In order for the hinge portions of the first and the second arms to engage each other to form the hinge mechanism, a hinge portion of one of the two arms may partially or completely overlap, cross, intersect, or interlock with, the hinge portion of the other of the two arms. Preferably said overlap, crossing, intersection or interlocking is essentially in the plane on which the first and the second arms rotate relative to each other about the hinge mechanism.

In some embodiments, while mutually engaged to each other, the hinge portions of the first and second arm are adapted to slide relative to each other along a direction substantially parallel to the clamping direction.

Another benefit of the invention is that the handle portions of the first and second arms make it possible to expand the cross-section of the cavity using one hand only, which allows the hollow elastic sleeve to be placed/attached to the body limb that is to be measured with a single hand. In this manner, the device of the present invention overcomes the drawback of known sleeve-type pulse oximetry probes, which require at least two hands to enlarge the opening of the sleeve through which the limb is received. A fringe benefit of this is that, by using the device of the present invention, the caregiver will not be tempted to hold the limb while measuring, so that the measurement will be less disturbed and the results will be more reliable.

In the context of the present invention, the term clamping direction preferably refers to a direction along which the coupling portions of the first and second arms clamp onto a limb that has been inserted into the cavity due to the resetting force of the hollow elastic sleeve in absence of any external force. Therefore, the clamping direction preferably corresponds to a direction that is essentially contained in the plane on which the first and the second arms rotate relative to each other about the hinge mechanism, while at the same time being essentially perpendicular to the longitudinal extension of the cavity (i.e., the direction along which the limb is to be received).

Preferably, the size of the cross-section can be adjusted from a minimum size where the hollow elastic sleeve is in its predetermined shape (i.e., not subjected to any external force), to a maximum size where the first and second arms are rotated to a maximum rotation angle relative to each other under the action of a compression force exerted on their handle portions. Said maximum rotation angle may be the angle for which the handle portions of the first and second arms just come into contact with each other.

The hollow elastic sleeve is preferably dimensioned so that the size of the cross-section of its cavity, when the sleeve is in its predetermined shape, is (slightly) smaller than the size of the limb (i.e., the size of the cross-section of the limb) for the youngest infant age group for which the device is intended. In this manner, even when smallest-sized limbs are inserted into the cavity, the resilience of the hollow elastic sleeve will exert a gentle force on the limb to enclose it in the cavity and secure it in place during the measurement.

In the context of the present invention, the cross-section of the cavity of the hollow elastic sleeve preferably refers to an orthogonal cross-section, that is, the shape of the cavity when taking a slice on a plane orthogonal to the longitudinal direction along which the cavity extends. Also in the context of the present invention, a size of the cross-section preferably refers to a diameter, a diagonal or a perimeter of the cross-section, or to an area enclosed by the perimeter of the cross-section.

The cross-section of the cavity is a closed shape. This further reduces the chance of erroneously attaching the device to body parts with too large size, or which are too broad for the device, such as a complete foot, a complete hand, a lip or an ear, for which the device is not meant to be used.

Preferably, the cross-section of the cavity is ring-shaped, such as for instance circular or elliptical, which is advantageous for facilitating the safe receiving of cylinder-shaped body parts. However, other shapes, including polygonal shapes, are equally possible.

In some embodiments, the coupling portion of the first and the second arm are adapted to be releasably coupled, respectively, to the first and the second longitudinal section of the hollow elastic sleeve. In this manner, the device can be assembled when it is to be used and can be subsequently disassembled for its cleaning and storage. By uncoupling the first and second arms from the hollow elastic sleeve, it is possible to sterilize those parts that are usually in contact with the patient skin, such as the hollow elastic sleeve, more often, or to replace those parts that are exposed to a higher tear and wear independently.

In such embodiments, each of the first and the second longitudinal sections of the hollow elastic sleeve preferably comprises a receptacle comprising an opening proximate to the proximal end, the receptacle being adapted to receive through said opening the coupling portion of a respective one of the first and the second arm. In this manner, the device can be assembled and disassembled more quickly. More importantly, as the position of the receptacles determines where the coupling portions of the first and second arms are to be inserted, the position of the receptacles serves as a reference for the caregiver to know the orientation of the clamping direction, and the position of the physiological sensor relative to said reference.

In some of these embodiments, the coupling portions of the first and second arms are differently shaped, and the receptacles in the first and second longitudinal sections of the hollow elastic sleeve are also differently shaped, each receptacle having a matching shape to that of its corresponding coupling portion. This makes it impossible to couple one of the two arms in the receptacle intended for the other arm, which advantageously provides additional guidance to the caregiver to know the relative positon and/or orientation of the physiological sensor arranged within the cavity with respect to the first and second arms.

Alternatively, in some other embodiments, the hollow flexible sleeve is overmolded on the coupling portion of the first and the second arm. In this way the arms are more securely coupled to the hollow elastic sleeve.

In such other embodiments, the device preferably further comprises a flexible member overmolded on the handle portion of the first and the second arm, the flexible member being connected to the hollow flexible sleeve at said proximal end. The flexible member protects the handle portions against tear and wear and provides a more comfortable touch. In addition, it also offers a better grip when actuating the handle portions of the two arms, preventing for example that the device slips off the caregiver's hand. To further increase the grip, the flexible member may comprise protrusions and/or grooves spread over an outer surface of said flexible member.

More preferably, the flexible member and the hollow flexible sleeve are formed integrally as a single piece. This not only makes fabrication of the device easier, but also avoids dirt or external components getting into the device and interfering, for instance, with the operation of the hinge mechanism.

In some embodiments, the cross-section of the cavity comprises a first and a second portion aligned with and spanning the width of, respectively, the first and the second longitudinal section of the hollow flexible sleeve, and two sidewall portions connecting each end of the first portion with a respective end of the second portion, wherein each of the two sidewall portions bends inwardly (i.e., away from the inner surface of the cavity) at least once when the hollow flexible sleeve is in its predetermined shape. The bellow-shaped sidewall portions advantageously improve the alignment of the limb received in the cavity with the physiological sensor. As the size of the limb received in the cavity increases, the cross-section of the cavity expands, and the sidewall portions are straightened (i.e. the bends become shallower). On the contrary, as the size of the limb received in the cavity decreases, the cross-section of the cavity shrinks, and the sidewall portions are folded (i.e. the bends become deeper). Since the bellow-shaped sidewall portions tend to occupy the remaining space inside the cavity not occupied by the limb, a self-centering mechanism is obtained that avoids erroneous positioning of the limb relative to the physiological sensor, thereby leading to more reliable $SpO_2$ measurements.

In these embodiments, the cross-section of the cavity is preferably symmetrical with respect to the clamping direction.

The hollow flexible sleeve may be configured to embed at least a part of the physiological sensor. Having the physiological sensor as an integrated part of the hollow flexible sleeve enables a compact device which can be used without being connected to external sensor optics, thus facilitating easy $SpO_2$ measurements.

In some embodiments, the hollow flexible sleeve further comprises a first and a second recess on respective diametrically-opposite inner surfaces of the cavity aligned with the clamping direction, and at least a part of the physiological sensor is provided in the first and the second recess. Besides a more effective utilization of space, this also increases the stability of the relative position between the limb and the sensor optics, so that the $SpO_2$ measurements are more accurate.

In these embodiments, the physiological sensor preferably comprises a light source for generating a measurement light signal and a light detector for detecting the measurement light signal after its interaction with the limb.

More preferably, the light source is provided in the first recess and the light detector is provided in the second recess. This enables $SpO_2$ measurements in transmission geometry where the light signal generated by the light source interacts with the limb by transmitting through it.

In other embodiments, the hollow flexible sleeve further comprises a recess on an inner surface of the cavity aligned with the clamping direction, and at least a part of the physiological sensor is provided in said recess. This enables $SpO_2$ measurements in a reflection geometry where the light signal generated by a light source of the sensor interacts with the limb by being reflected on a surface of the latter. The sensor also comprises a light detector located at the same side of the limb inside the cavity as the light source. In particular, the light source and the light detector are preferably separated from each other with a spacing of 2 to 10 mm, and more preferably of 3 to 7 mm. The light reaching the light detector may have advantageously been scattered inside the limb such that the light is backscattered into the direction of the light detector.

The hollow elastic sleeve may optionally be made of a material comprising foam or silicone (such as, for instance, silicone rubber). These materials provide very good mechanical properties such as elasticity, resistance and durability, which makes them well suited for the device of the present invention. At the same time, these materials also offer good properties for medical applications. For example, they are inert and have a high temperature resistance, which facilitate the sterilization of devices or components made of such materials. Finally, from a manufacturing standpoint, they are inexpensive, versatile, and compatible with molding, extrusion or machining processes.

On the other hand, the first and second arm are preferably made of a rigid or semi-rigid material, more preferably a plastic material such as polypropylene (PP), acrylonitrile butadiene styrene (ABS), acrylonitrile butadiene styrene/polycarbonate (ABS/PC), or polyamide (PA). Moreover, additives can be optionally added to these materials to enhance their properties.

When an overmolding, or "two shot" (or 2K) injection molding process is used for manufacturing the device, it is important that the selection of materials for forming the hollow elastic sleeve and the two arms have an adequate chemical bonding. In a preferred embodiment, the hollow elastic sleeve is made of a material comprising silicone, and the first and second arms are made of a material comprising ABS. In another preferred embodiment, the hollow elastic sleeve is made of a material comprising a thermoplastic elastomer (TPE), and the two arms are made of a material comprising PP. The specific combination of materials of these two embodiments bond chemically well to each other.

The hollow elastic sleeve may preferably comprise a blocking element for limiting the receivable depth of the limb in the cavity, the blocking element being arranged across the cross-section of the cavity, proximate to the proximal end of the hollow elastic sleeve. This advantageously prevents the limb, e.g. a finger, from going completely through the entire extension of the cavity of the hollow elastic sleeve, thereby reducing the risk of entrapment of the limb with, for instance, the hinge mechanism.

Another aspect of the present invention relates to a method for manufacturing a device for measuring a physiological parameter of a human limb. The method comprises the steps of:

providing a hollow elastic sleeve comprising a cavity adapted to enclose the limb, the cavity extending longitudinally between a distal end and a proximal end and having a closed-loop cross-section, the hollow elastic sleeve having a predetermined shape to which the sleeve returns due to its resilience when an external force deforming the sleeve ceases to be applied thereto;

coupling a coupling portion of a first and a second arm, respectively, to a first and a second longitudinal section of the hollow elastic sleeve from said proximal end, the first and second longitudinal sections being diametrically opposite to each other along a clamping direction extending across the cross-section of the cavity, wherein each arm further comprises a handle portion and a hinge portion located at an intermediate position of the arm between the coupling portion and the handle portion; and arranging a physiological sensor within the cavity of the hollow elastic sleeve, the physiological sensor being configured for interacting with the limb enclosed in said cavity; and wherein the hollow sleeve holds the first and the second arms and causes the hinge portions of the first and the second arm to each other to form a hinge mechanism so that, by applying a compression force on the handle portion of the first and second arms, the first and second arms rotate relative to each other about the hinge mechanism expanding the cross-section of the cavity at said distal end, thereby allowing the limb to be received in the cavity through said distal end, and, by ceasing said compression force, the resilience of the hollow elastic sleeve causes the first and second arms to rotate relative to each other in the opposite direction than following compression, thereby enclosing the limb in the cavity.

In accordance with the present invention the hinge portions of the first and second arms, when engaged to each other, are further configured to slide relative to each other, so that the separation between the first and second arms along said clamping direction can be adjusted.

All above alternatives of the present invention enable accurate $SpO_2$ measurements independent on the size of the limb, in particular for infants. The present invention therefore overcomes, or at least reduces, the drawbacks caused by unsatisfactory positioning of the device while attaching it to a patient, e.g. positioning the clip designed for being attached to a finger or toe to a different body part which is not optimal for $SpO_2$ measurements. The positioning of the limb relative to the device after being received in the cavity is easier compared to known devices. The present invention also improves the alignment of the limb relative to the physiological sensor resulting in more reliable $SpO_2$ measurements.

BRIEF DESCRIPTION OF THE DRAWINGS

In the following some preferred embodiments of the invention will be described with reference to the enclosed figures. They are provided for illustration purposes only without however limiting the scope of the invention.

FIG. 1 shows a device according to a first embodiment of the present invention: (a) perspective view; (b) side view; and (c) exploded side view;

FIG. 2 shows a device in accordance to a second embodiment of the present invention: (a) perspective view; and (b) side view;

FIG. 3 shows a device according to a third embodiment of the present invention: (a) perspective view; and (b) side view;

DETAILED DESCRIPTION OF THE INVENTION

The invention solves the above problems by providing a device with improved positioning of the limb in the cavity of the hollow elastic sleeve.

Figure 1:
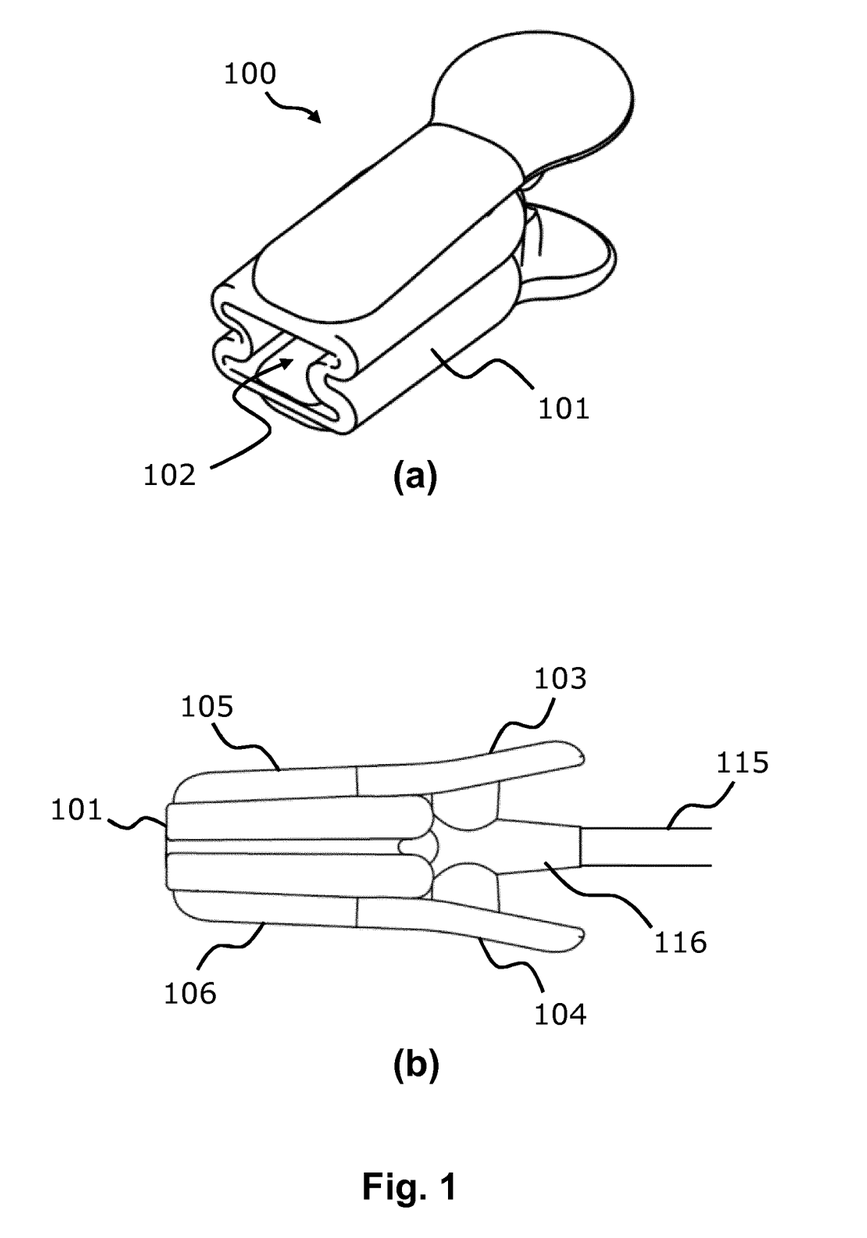
Figure 1C:
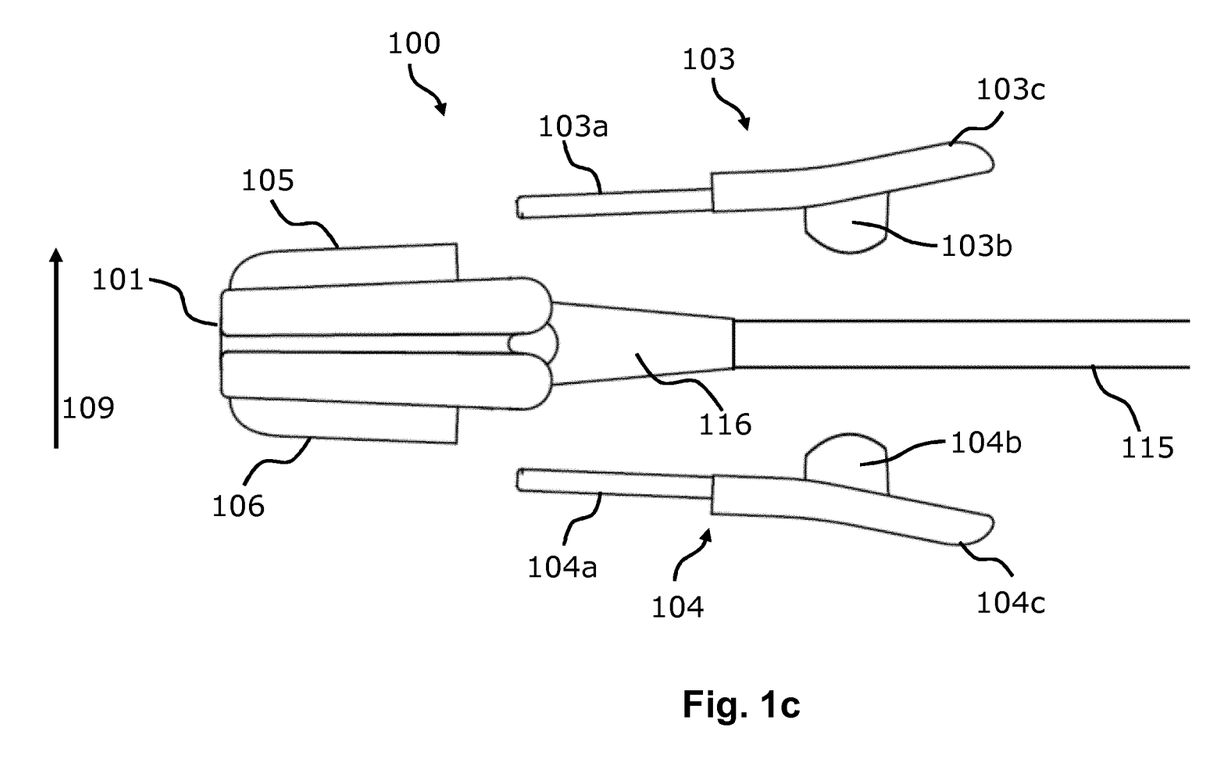

FIGS. 1a-c show different views of a first embodiment of a device for measuring a physiological parameter of a human limb according to the present invention. In particular, the device 100 comprises a hollow elastic sleeve 101 comprising a cavity 102 that is adapted to enclose the limb, such as a finger of a patient. The cavity 102 extends longitudinally between a distal end and a proximal end and has a closed-loop cross-section.

In this example, the distal end is the one that appears in front (i.e. on the first plane) in the perspective view of FIG. 1a or in the left in the side view of FIG. 1b. That end is "distal" with respect to the position of the caregiver or medical practitioner that operates the device, because that end is located farther from him or her when holding the device. Said distal end is, at the same time, the end of the cavity 102 of the hollow elastic sleeve closer to the patient, through which the patient's limb is received. On the other hand, the proximal end, although not visible in the FIG. 1, is the one that is closer to the caregiver or medical practitioner that operates the device, and would be located in the rear of the hollow elastic sleeve 101 in the perspective view of FIG. 1a or, on the right side of the sleeve 101 in the side view of FIG. 1b.

The device 100 also comprises a first and a second arm 103, 104, each comprising a hinge portion 103b, 104b located at an intermediate position of the arm between a coupling portion 103a, 104a and a handle portion 103c, 104c. This can be better appreciated in the exploded side view of FIG. 1c. The coupling portion 103a, 104a of the first and the second arm can be releasably coupled, respectively, to a first and a second longitudinal section of the hollow elastic sleeve from said proximal end. For that purpose, the first and the second longitudinal sections of the hollow elastic sleeve comprise a receptacle 105, 106 that comprises an opening proximate to the proximal end. In this manner, the receptacles can receive through said opening, respectively, the coupling portions 103a, 104a of the first and the second arm.

With reference to FIGS. 1b and 1c, the first longitudinal section is on upper side of the cavity 102 (and hence receptacle 105 is on the upper side of the hollow elastic sleeve 101) and the second longitudinal section is on the bottom side of the cavity 102 (and, accordingly, receptacle 106 is on the bottom side of sleeve 101). Therefore, said first and second longitudinal sections are diametrically opposite to each other along a clamping direction 109—the vertical direction in FIGS. 1b and 1c—that extends across the cross-section of the cavity 102.

Finally, although not visible in the example of FIG. 1, the device 100 also comprises a physiological sensor arranged within the cavity 102 of the hollow elastic sleeve and configured for interacting with the limb enclosed in said cavity. However, it is represented in FIGS. 1b and 1c the cable 115 that includes the electrical conductors that interconnect the physiological sensor with external control electronics. The cable 115 comprises a connecting portion 116 with a tapering profile (e.g. frustoconical) that interfaces with the hollow elastic sleeve 101.

The hollow elastic sleeve 101 is made of silicone rubber and has a predetermined shape to which the sleeve returns due to its resilience when an external force deforming the sleeve ceases to be applied thereto and, as it can be observed in FIG. 1a, the opening at the distal end of the cavity 102 has a cross-section, in particular an orthogonal cross-section that is ring-shaped defining a closed loop. The perimeter of said cross-section resembles a Greek character "Sigma" (Σ) joined at its upper and bottom segments to a mirror-like version of the same Greek character. As a result, the cross-section of the cavity 102 is symmetrical with respect to clamping direction 109, with essentially straight top and bottom portions and two sidewall portions that bend inwardly once when the hollow flexible sleeve is in its predetermined shape.

When the first and the second arms are coupled to the hollow elastic sleeve 101, the hollow elastic sleeve holds the first and the second arms 103, 104 and causes the hinge portions 103b, 104b of the first and the second arms to engage each other, in this particular example, through the connecting portion 116 to form a hinge mechanism. In this manner, by applying a compression force on the handle portion 103c, 104c of the first and second arms, the first and second arms 103, 104 rotate relative to each other about the hinge mechanism expanding the cross-section of the cavity 102 at said distal end, thereby allowing the limb to be received in the cavity through said distal end, and, by ceasing said compression force, the resilience of the hollow elastic sleeve 101 causes the first and second arms 103, 104 to rotate relative to each other in the opposite direction than following compression, thereby enclosing the limb in the cavity 102. Moreover, the hinge portions 103b, 104b of the first and second arms, when engaged to each other, are further configured to slide relative to each other due, in this example, to the tapering profile of the connecting portion 116, so that the separation between the first and second arms 103, 104 along said clamping direction 109 can be adjusted.

Figure 2:
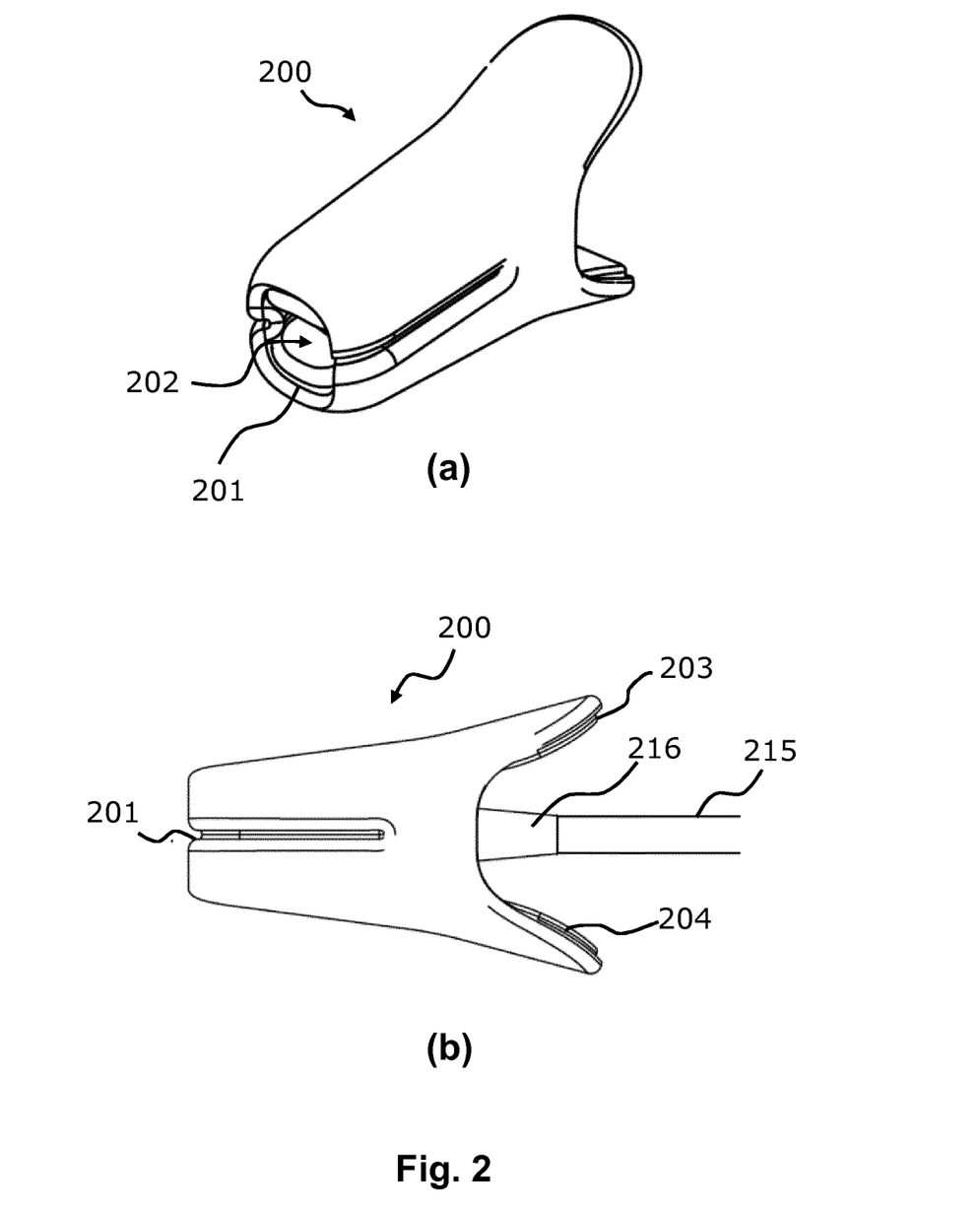

Referring now to FIGS. 2a and 2b, it is there depicted a second embodiment of a device in accordance with the present invention. As in the previous example shown in FIG. 1, the device 200 also comprises a hollow elastic sleeve 201 that includes a cavity 202 having a closed-loop cross-section and that extends longitudinally between a distal end 207 and a proximal end 208. The device 200 also comprises a first and a second arm 203, 204, with each arm comprising a hinge portion 203b, 204b located at an intermediate position of the arm between a coupling portion 203a, 204a and a handle portion 203c, 204c. But, conversely, to the previous example, the hollow elastic sleeve 201 is now overmolded on the first and the second arm 203, 204. This can be better observed in FIG. 4, which presents a cut-out view of the device 200 of FIG. 2 sliced along a plane defined by the longitudinal direction along which the cavity extends and the clamping direction 209 (i.e., a plane parallel to the paper for the side view of FIG. 2b), and in which the hollow elastic sleeve 201 extends over the outer faces of the coupling portion 203a, 204a and the handle portion 203c, 204c of both arms. However, the inner faces of the handle portions 203c, 204c are not covered by the hollow elastic sleeve 201 and remain exposed. Thus, the device 200 is an exemplary embodiment of a partially-overmolded solution.

FIGS. 3a and 3b illustrate different views of a fully-overmolded solution, in which a device 300 comprises a hollow elastic sleeve 301 overmolded on the coupling portion of a first and a second arm (not represented in the figures). However, conversely to the example in FIG. 2, the device 300 further comprises a flexible member 311 overmolded on the handle portion of the first and the second arm.

The hollow elastic sleeve 301 comprises a cavity adapted to enclose the limb, the cavity having a closed-loop cross-section and extending longitudinally between a distal end and a proximal end. As in the previous figures, the distal end appears on the first plane in the perspective view of FIG. 3a or in the left in the side view of FIG. 3b, while the proximal end would be farther in the rear in FIG. 3a and towards the right in FIG. 3b. In fact the position of the proximal end would be around the dashed line depicted in FIG. 3b.

The flexible member 311 is connected to the hollow flexible sleeve 301 at the proximal end of the latter. In the figure, said connection is indicated by means of the dashed line. Although in this example the flexible member 311 and the hollow flexible sleeve 301 are formed integrally as a single piece, in other examples the they can be two separate pieces connected to each other (e.g. by press-fit coupling of the flexible member 311 on the proximal end of the hollow flexible sleeve 301).

Figure 4:
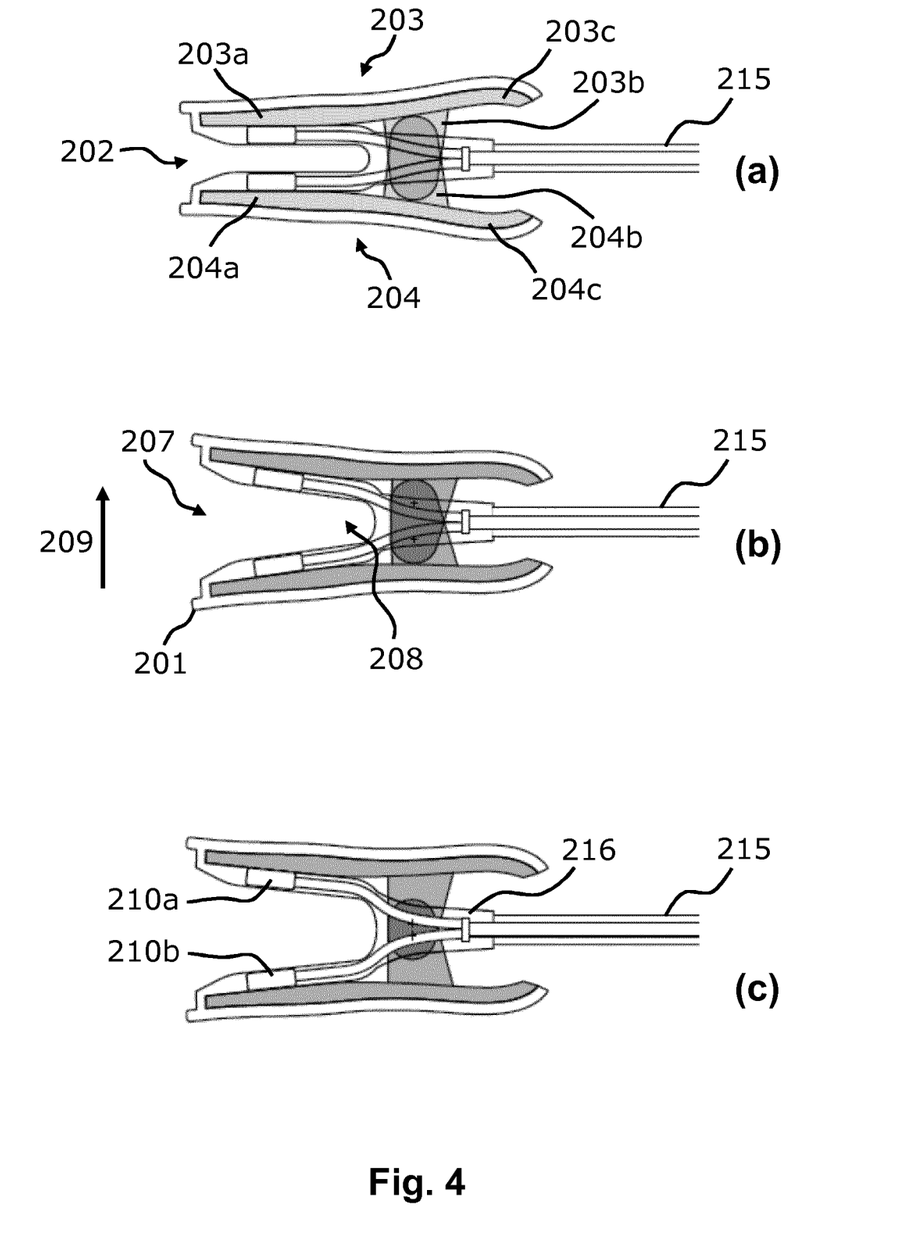
FIGS. 4a-c schematically represent different time instants of the operation of the device of FIG. 2 to clamp on a limb.

The operation of the device according to the present invention is illustrated in FIG. 4 with reference to the device 200 described in the context of FIG. 2. In that respect, FIGS. 4a-c show the position of the first arm 203 relative to the second arm 204, and the deformation that the hollow elastic member 201 undergoes, at different time instants of the operation of the device 200 in order to receive a limb into the cavity of the sleeve and secure it place during measurement.

The device 200 comprises a physiological sensor embedded in the hollow flexible sleeve 201 and that comprises a light source 210a for generating a measurement light signal and a light detector 210b for detecting the measurement light signal after its interaction with the limb. The light source 210a is provided in a first recess on an inner surface of the cavity 202 just below the coupling portion 203a of the first arm, while the light detector 210b is provided in a second recess just above the coupling portion 204a of the second arm. That is, the light source 210a and the light detector 210b are in respective recesses on diametrically-opposite inner surfaces of the cavity, said surfaces being aligned with the clamping direction 209. A cable 215 includes the electrical conductors that interconnect the light source 210a and the light detector 210b with external control electronics. As in the example described in the context of FIG. 1, the cable 215 also comprises a connecting portion 216 with a tapering profile for interfacing with the hollow elastic sleeve 201 at the proximal end 208.

It can be observed in the figures that the cavity 202 is closed at its proximal end 208. Indeed, a portion of the flexible material of the hollow elastic sleeve 201 at the interface with the connecting portion 216 of the cable 215 acts at the same time as a blocking element that limits the receivable depth of the limb in the cavity 202, preventing the limb from becoming entrapped with the hinge mechanism.

Referring now to FIG. 4a, it is there shown the device 200 in its "initial state", when no compression force is applied on the handle portions 203c, 204c of the first and second arms. The hollow elastic sleeve 201 is, thus, in its predetermined shape, biasing the coupling portions 203a, 204a of the first and second arms so as to close in toward each other. As a result, in such initial state, the separation between the coupling portions 203a, 204a along the clamping direction 209 is the smallest possible and, accordingly, the size of the cross-section of the cavity 202 of the hollow elastic sleeve 201 is at its minimum.

When the first and the second arms 203, 204 are coupled to the hollow elastic sleeve 201, the hollow elastic sleeve holds the first and the second arms and causes the hinge portions 203b, 204b of the first and the second arm to engage each other to form a hinge mechanism. In particular, each hinge portion comprises a tab with a base connected to the respective arm and that projects away from an inner surface of said arm to an end with a rounded shape. While in such initial state, the resilience of the hollow elastic sleeve 201 keeps the rounded end of the tab of each arm pressed against the inner surface of the other arm. The projecting tabs make it possible to achieve the mutual engagement of the two hinge portions, while allowing the connecting portion 216 of the cable 215 to pass through them.

FIG. 4b represents the situation when a compression force that exceeds the resetting force of the hollow elastic sleeve 201 is applied on the handle portion 203c, 204c of the first and second arms, in which case the first arm 203 and second arm 204 rotate relative to each other about the hinge mechanism thanks to the rounded ends of the tabs. This rotation increases the separation between the coupling portions 203a, 204a of the two arms, expanding the cross-section of the cavity 202 at its distal end 207 and facilitating a loose insertion of the limb (not represented in the figure) into the cavity 202 from said distal end.

By ceasing the compression force once the limb has been inserted to a desired depth along the cavity, the resilience of the hollow elastic sleeve 201 exerts a resetting force on the coupling portions 203a, 204a of the two arms that tends to bring them closer to each other. Once again, the rounded ends of the tabs in the hinge portions 203b, 204b allow the relative rotation of the arms 203, 204 in the opposite direction than following compression. This results in a reduction of the cross-section of the cavity 202 near its distal end 207, securing the inserted limb in place.

In accordance with the present invention, the device 200 is capable of adjusting the size of the cross-section of the cavity 202 to match the size of the infant's limb. This is possible by having a slidable engagement of the hinge portions, as illustrated in FIG. 4c.

The hollow elastic sleeve 201 is dimensioned so that the size of the cross-section of its cavity 202, when the sleeve is in its predetermined shape, is smaller than the size of the limb. This means that, as the first and second arms 203, 204 rotate back towards the initial state when the compression force has ceased, at some point they will collide with the limb. At that point, the tabs of the hinge portions 203b, 204b start sliding with respect to each other along a direction substantially parallel to the clamping direction 209, so that the rounded end of the tab of each arm is no longer in contact the inner surface of the other arm, which in turn increases the separation between the two arms and, by doing so, enables further rotation of the two arms to reach a position more parallel to the inserted limb and, hence, obtain a better contact of the light source 210a and light detector 210b on the skin of the limb. Therefore, FIG. 4c depicts a "final state"

in which the limb is securely clamped in the device 200 and ready for a SpO$_2$ measurement.

Figure 3:
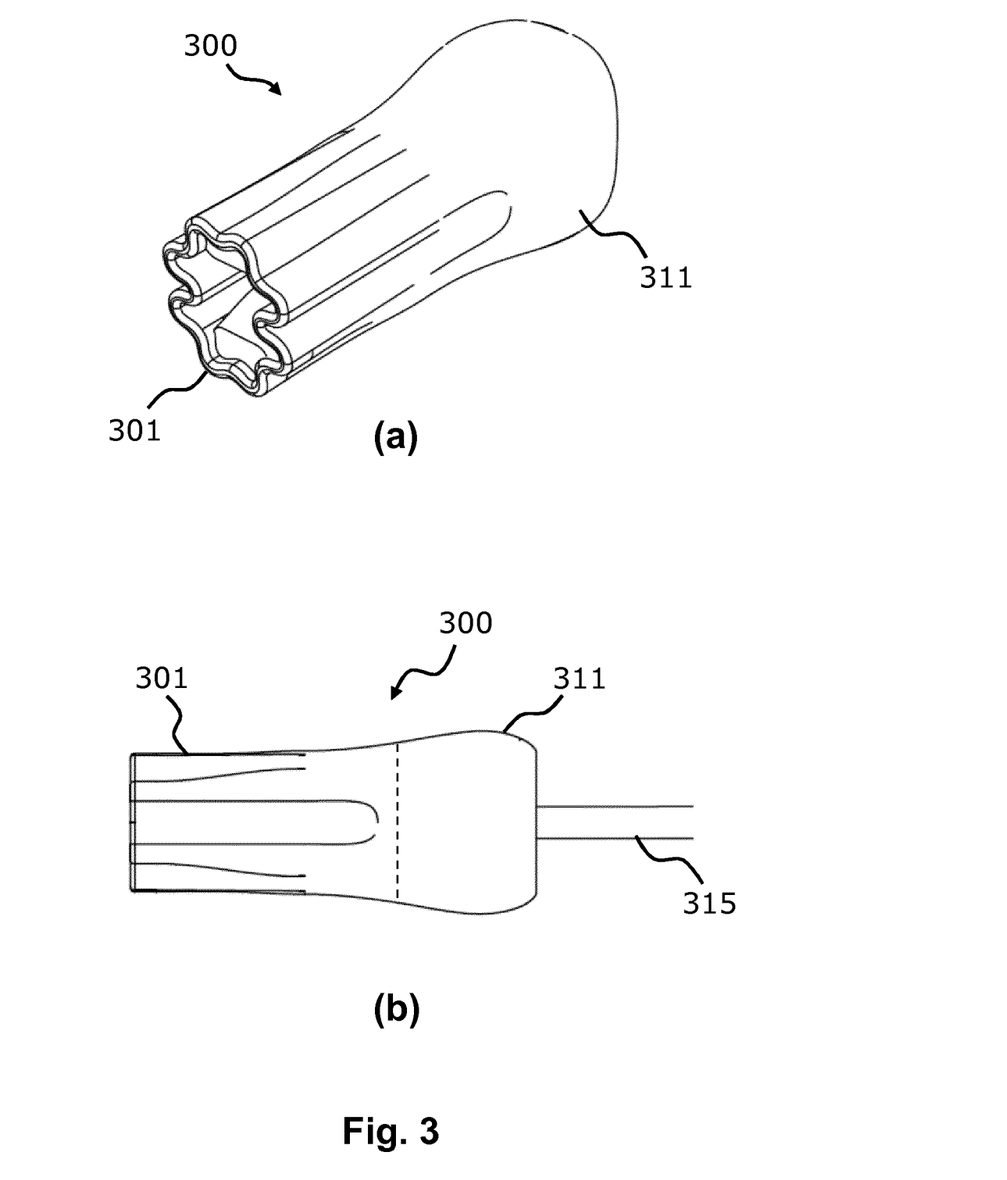
Figure 5:
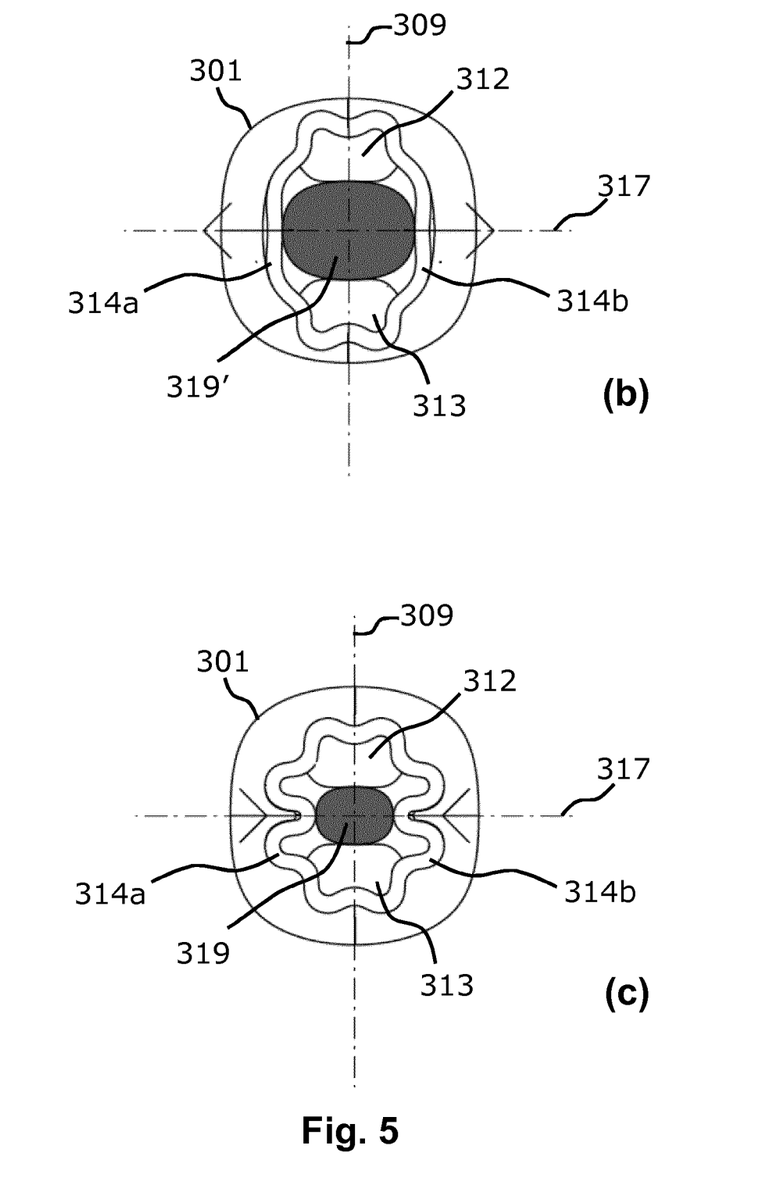
FIGS. 5a-c depict how the cross-section of the cavity of the hollow elastic sleeve of the device of FIG. 3 adapts to limbs of different sizes.
Figure 5A:
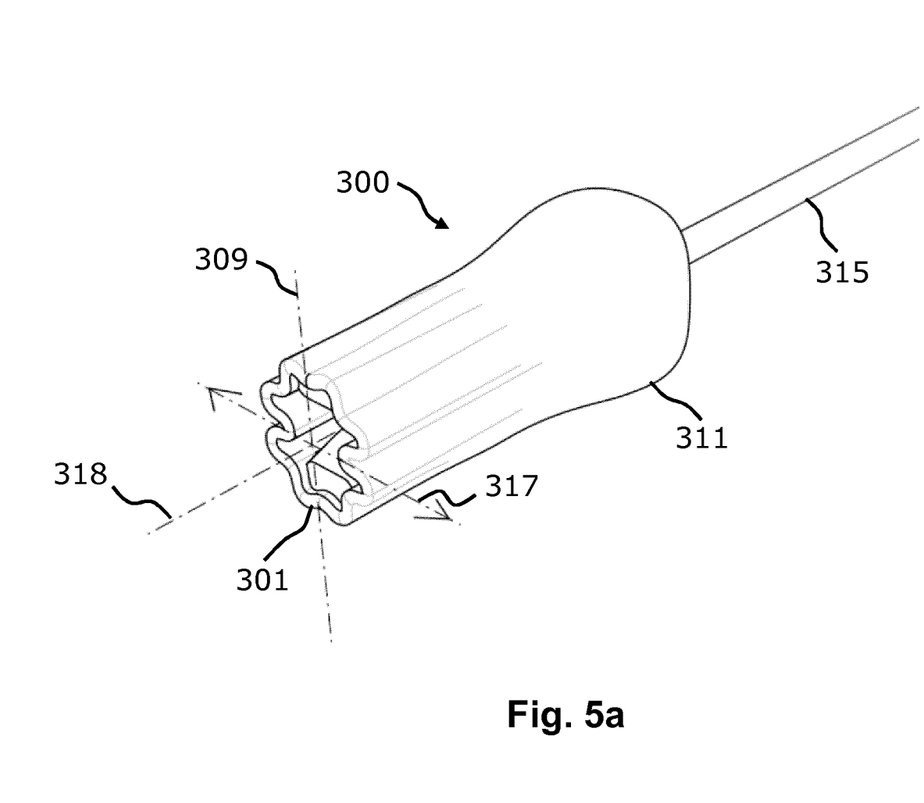

In FIGS. 5a-c it is schematically represented how the cross-section of the hollow elastic sleeve 301 of the device in FIG. 3 can adapt to limbs of different sizes. FIG. 5a shows a perspective view of the device 300 in relation to a coordinate axes system. The hollow elastic sleeve 301 and cable 315 are oriented along a longitudinal axis 318, along which the cavity included in the sleeve 301 extends. The cross-section of the cavity is then contained in a plane defined by a vertical axis 309 (which corresponds to the clamping direction) and a transversal axis 317 (the horizontal axis in FIGS. 5b and 5c).

FIGS. 5b and 5c provide a frontal view of the device 300, as seen from the distal end of the cavity of the hollow elastic sleeve 301, with the vertical and horizontal axes corresponding, respectively, to the clamping direction 309 and the transversal axis 317. The cross-section of said cavity defines a closed loop comprising a first portion 312 and a second portion 313 centered on the clamping direction 309, and two sidewall portions 314a, 314b connecting each end of the first portion 312 with a respective end of the second portion 313. The first and second portions 312, 313 are aligned with, and span the width of, the longitudinal sections of the hollow flexible sleeve 301 to which the first and second arms of the device 300 are coupled.

The sidewall portions 314a, 314b are meander-shaped or bellow-shaped, bending inwardly at least once, which make it possible to adapt the cross-section of the cavity to limbs of different sizes and, at the same, center the limb with respect to the physiological sensor. For a large limb 319', as illustrated in FIG. 5b, the cross-section of the cavity needs to expand significantly with respect to the situation in which no limb is inserted and the hollow elastic sleeve 301 is in its predefined shape. Then, as the first and second arms of the device are separated along the clamping direction 309, the sidewall portions 314a, 314b are straightened (i.e. the bends become shallower along the transversal axis 317). On the other hand, FIG. 5c shows the case in which a small-sized limb 319 is received in the cavity, in which the cross-section of the cavity does not need to be expanded as much as in the previous case. Therefore, as the first portion 312 and the second portion 313 remain closer to each other along the clamping direction 309, the sidewall portions 314a, 314b preserves deeper bends along the transversal axis 317. That is, the bellow-shaped sidewall portions 314a, 314b tend to occupy the remaining space inside the cavity not occupied by the limb.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device for measuring a physiological parameter of a subject, comprising:
    a hollow elastic sleeve comprising a cavity adapted to enclose a limb of the subject, the cavity extending longitudinally between a distal end and a proximal end and having a closed-loop cross-section, the hollow elastic sleeve having a predetermined shape to which the sleeve returns due to its resilience when an external force deforming the sleeve ceases to be applied thereto;
    a first and a second arm, each arm comprising a hinge portion located at an intermediate position of the arm between a coupling portion and a handle portion, the coupling portion of the first and the second arm being adapted to be coupled, respectively, to a first and a second longitudinal section of the hollow elastic sleeve from said proximal end, the first and second longitudinal sections being diametrically opposite to each other along a clamping direction extending across the cross-section of the cavity; and
    a physiological sensor arranged within the cavity of the hollow elastic sleeve and configured for interacting with the limb enclosed in said cavity;
    wherein, when the first and the second arms are coupled to the hollow elastic sleeve, the hollow elastic sleeve holds the first and the second arms and causes the hinge portions of the first and the second arms to engage each other to form a hinge mechanism so that, by applying a compression force on the handle portion of the first and second arms, the first and second arms rotate relative to each other about the hinge mechanism expanding the cross-section of the cavity at said distal end, thereby allowing the limb to be received in the cavity through said distal end, and, by ceasing said compression force, the resilience of the hollow elastic sleeve causes the first and second arms to rotate relative to each other in the opposite direction than following compression, thereby enclosing the limb in the cavity; and
    wherein the hinge portions of the first and second arms, when engaged to each other, are further configured to slide relative to each other along a tapered connecting portion, so that the separation between the first and second arms along said clamping direction can be adjusted.

2. The device according to claim 1, wherein the coupling portion of the first and the second arm are adapted to be releasably coupled, respectively, to the first and the second longitudinal section of the hollow elastic sleeve.

3. The device according to claim 2, wherein each of the first and the second longitudinal sections of the hollow elastic sleeve comprises a receptacle comprising an opening proximate to the proximal end, the receptacle configured to receive through said opening the coupling portion of a respective one of the first and the second arm.

4. The device according to claim 1, wherein the hollow flexible sleeve is overmolded on the coupling portion of the first and the second arm.

5. The device according to claim 4, further comprising a flexible member overmolded on the handle portion of the first and the second arm, the flexible member being connected to the hollow flexible sleeve at said proximal end.

6. The device according to claim 5, wherein the flexible member and the hollow flexible sleeve are formed integrally as a single piece.

7. The device according to claim 1, wherein the cross-section of the cavity comprises a first and a second portion aligned with and spanning the width of, respectively, the first and the second longitudinal section of the hollow flexible sleeve, and two sidewall portions connecting each end of the first portion with a respective end of the second portion, wherein each of the two sidewall portions bends inwardly at least once when the hollow flexible sleeve is in its predetermined shape.

8. The device according to claim 7, wherein the cross-section of the cavity is symmetrical with respect to the clamping direction.

9. The device according to claim 1, wherein the hollow flexible sleeve is configured to embed at least a part of the physiological sensor.

10. The device according to claim 1, wherein the hollow flexible sleeve further comprises a first and a second recess on respective diametrically-opposite inner surfaces of the cavity aligned with the clamping direction, and wherein at least a part of the physiological sensor is provided in the first and the second recess.

11. The device according to claim 10, wherein the physiological sensor comprises a light source for generating a measurement light signal and a light detector for detecting the measurement light signal after its interaction with the limb.

12. The device according to claim 11, wherein the light source is provided in the first recess and the light detector is provided in the second recess.

13. The device according to claim 1, wherein the hollow elastic sleeve is made of a material comprising foam or silicone.

14. The device according to claim 1, wherein the hollow elastic sleeve comprises a blocking element for limiting the receivable depth of the limb in the cavity, the blocking element being arranged across the cross-section of the cavity, proximate to the proximal end of the hollow elastic sleeve.

15. A method for manufacturing a device for measuring a physiological parameter of a subject, comprising the steps of:
providing a hollow elastic sleeve comprising a cavity adapted to enclose a limb of the subject, the cavity extending longitudinally between a distal end and a proximal end and having a closed-loop cross-section, the hollow elastic sleeve having a predetermined shape to which the sleeve returns due to its resilience when an external force deforming the sleeve ceases to be applied thereto;
coupling a coupling portion of a first and a second arm, respectively, to a first and a second longitudinal section of the hollow elastic sleeve from said proximal end, the first and second longitudinal sections being diametrically opposite to each other along a clamping direction extending across the cross-section of the cavity, wherein each arm further comprises a handle portion, and a hinge portion located at an intermediate position of the arm between the coupling portion and the handle portion; and
arranging a physiological sensor within the cavity of the hollow elastic sleeve, the physiological sensor being configured for interacting with the limb enclosed in said cavity;
wherein the hollow sleeve holds the first and the second arms and causes the hinge portions of the first and the second arm to each other to form a hinge mechanism so that, by applying a compression force on the handle portion of the first and second arms, the first and second arms rotate relative to each other about the hinge mechanism expanding the cross-section of the cavity at said distal end, thereby allowing the limb to be received in the cavity through said distal end, and, by ceasing said compression force, the resilience of the hollow elastic sleeve causes the first and second arms to rotate relative to each other in the opposite direction than following compression, thereby enclosing the limb in the cavity;
wherein the hinge portions of the first and second arms, when engaged to each other, are further configured to slide relative to each other along a tapered connecting portion, so that the separation between the first and second arms along said clamping direction can be adjusted.

16. The method according to claim 15, further comprising, releasably coupling the coupling portion of the first and the second arm, respectively, to the first and the second longitudinal section of the hollow elastic sleeve.

17. The method according to claim 16, further comprising wherein each of the first and the second longitudinal sections of the hollow elastic sleeve comprises a receptacle comprising an opening proximate to the proximal end, receiving through said opening the coupling portion of a respective one of the first and the second arm.

18. The method according to claim 15, further comprising overmolding the hollow flexible sleeve onto the coupling portion of the first and the second arm.

19. The method according to claim 15, further comprising overmolding a flexible member onto the handle portion of the first and the second arm, the flexible member being connected to the hollow flexible sleeve at said proximal end.

20. The method according to claim 15, wherein the cross-section of the cavity comprises a first and a second portion aligned with and spanning the width of, respectively, the first and the second longitudinal section of the hollow flexible sleeve, and two sidewall portions connecting each end of the first portion with a respective end of the second portion, bending each of the two sidewall portions inwardly at least once when the hollow flexible sleeve is in its predetermined shape.

* * * * *